(12) United States Patent
Bahs et al.

(10) Patent No.: US 7,287,414 B2
(45) Date of Patent: Oct. 30, 2007

(54) PROCESS FOR MEASURING THE CONCENTRATION OF GASES

(75) Inventors: Hans-Jürgen Bahs, Ratekau (DE); Mladen Schlichte, Lübeck (DE); Matthias Martens, Gross Schenkenberg (DE); Andreas Sürig, Krummesse (DE); Wilfried Diekmann, Lübeck (DE)

(73) Assignee: Dräger Safety AG & Co. KGaA (DE)

( * ) Notice: Subject to any disclaimer, the term of this patent is extended or adjusted under 35 U.S.C. 154(b) by 0 days.

(21) Appl. No.: 11/370,571

(22) Filed: Mar. 8, 2006

(65) Prior Publication Data

US 2006/0266103 A1 Nov. 30, 2006

(30) Foreign Application Priority Data

May 27, 2005 (DE) .................. 10 2005 024 394

(51) Int. Cl.
*G01N 25/18* (2006.01)
(52) U.S. Cl. .................................... 73/25.03
(58) Field of Classification Search ............... 73/25.03, 73/25.05
See application file for complete search history.

(56) References Cited

U.S. PATENT DOCUMENTS

| | | | |
|---|---|---|---|
| 4,457,954 A | 7/1984 | Dabill et al. | |
| 4,551,425 A * | 11/1985 | Zemel | 435/4 |
| 4,583,070 A | 4/1986 | Okayama | |
| 4,668,635 A * | 5/1987 | Forster | 436/134 |
| 4,804,632 A | 2/1989 | Schuck et al. | |
| 4,861,557 A | 8/1989 | McNally | |
| 5,234,837 A * | 8/1993 | Accorsi et al. | 436/159 |
| 5,304,976 A | 4/1994 | Ono | |
| 5,513,125 A * | 4/1996 | Kauschke | 702/24 |
| 5,709,792 A * | 1/1998 | Zdanevitch et al. | 205/775 |
| 6,442,994 B1 * | 9/2002 | Slater | 73/23.31 |
| 6,742,382 B2 * | 6/2004 | Warburton et al. | 73/23.31 |
| 6,888,467 B2 * | 5/2005 | Green et al. | 340/632 |

FOREIGN PATENT DOCUMENTS

| | | |
|---|---|---|
| DE | 31 31 710 | 5/1982 |
| DE | 43 30 603 | 4/1994 |
| DE | 43 11 605 | 12/1994 |
| DE | 690 20 343 | 3/1996 |
| EP | 0 234 251 | 9/1987 |
| GB | 2 083 630 | 3/1982 |
| JP | 63169547 | * 7/1988 |
| WO | WO91/06849 | * 5/1991 |

* cited by examiner

*Primary Examiner*—Michael Cygan
(74) *Attorney, Agent, or Firm*—McGlew and Tuttle, PC

(57) ABSTRACT

A process is provided for measuring a gas concentration with at least one thermal measuring element. The thermal measuring element is operated by pulses. A measured value of the gas concentration in the environment of the measuring element is obtained from the evaluation of the response of the measuring element to at least one single pulse by determining transient states of the thermal measuring element. From this the measured value of the gas concentration in the environment of the measuring element can be derived, during the imposed pulse based on electric measured variables.

1 Claim, 5 Drawing Sheets

PROCESS FOR MEASURING THE CONCENTRATION OF GASES

CROSS REFERENCE TO RELATED APPLICATIONS

This application claims the benefit of priority under 35 U.S.C. § 119 of German Patent Application DE 10 2005 024 394.0 filed May 27, 2005, the entire contents of which are incorporated herein by reference.

FIELD OF THE INVENTION

The present invention pertains to a process for measuring the concentration of gases by means of thermal measuring elements.

BACKGROUND OF THE INVENTION

Processes for measuring the concentration of gases with thermal measuring elements are known per se. As a rule, the thermal behavior of the measuring element is observed by evaluating electric measured variables. The thermal behavior of the measuring element depends in different ways on the concentrations of different gases in the environment of the measuring element.

It is known that such processes can be carried out with so-called pellistors, which are partially catalytically active (U.S. Pat. No. 4,457,954, GB 2083630, U.S. Pat. No. 4,583,070). Two pellistors are usually used in case of the catalytic principle of measurement, one pellistor being prepared catalytically, while the second pellistor does not have this catalytic preparation.

The behavior of the catalytically prepared pellistor to change its resistance, which is characteristic of the gas to be detected, compared to the second, unprepared pellistor can be evaluated by means of a prior-art resistance bridge.

Various operating processes, such as constant-current, constant-voltage or constant-resistance processes, are known per se. The drawback of these processes in continuous operation is the high power consumption, which may be between 250 mW and 700 mW.

The following patent specifications U.S. Pat. No. 4,861,557, DE 4330603 and DE 3131710 describe processes with a pellistor bridge. The drawbacks of such processes are the complicated apparatus required for two measuring elements, the actuation thereof in a continuous mode of operation, and the high power requirement associated therewith.

A process with low power consumption is known, in which combustible gases are detected with only one measuring element (EP 0234251 A1). The gas concentration is determined in two stationary measurement phases according to this process.

The drawbacks of this process are that interfering environmental effects, e.g., temperature, pressure or moisture, are not compensated, and the power consumption is still very high for the operation in two measurement phases.

It is known that thermal measuring elements can be operated cyclically, in which case three different phases of operation alternate regularly (DE 69020343 T2). A heating phase is first carried out, during which the measuring element is heated to a preset resistance. This is followed by the measurement phase, during which the measuring element is maintained at a constant resistance value. This is followed by a rest phase, during which the measuring element is adjusted to a static resistance. A Pt air-core coil with a wire diameter of 80 μm is mentioned as the measuring element. The working temperature of the resistor element is therefore selected to be such that the temperature set point of the Pt coil is in the range of 570° C. to 1,100° C. By contrast, the use of pellistors was rejected, mainly because of the thermal inertia of the pellistor beads and the limited long-term stability. The drawback of this process is that the Pt air-core coils also have an excessively low long-term stability at such high operating temperatures and a relatively high power consumption is also associated with the high operating temperature.

Furthermore, it is known that the impression of an excitation function and evaluation of the response function can be used to determine the percentage of combustible gases in a gas mixture as well as to classify them according to gas classes (DE 4311605 C1). Depending on the selected function, the effort needed for control and evaluation may be high.

SUMMARY OF THE INVENTION

The object of the present invention is to provide a process that makes it possible with little effort to carry out gas concentration measurements with the smallest possible amount of energy.

According to the invention, a process is provided for measuring the gas concentration with at least one thermal measuring element, which is operated by pulses. A measured value of the gas concentration in the environment of the measuring element is obtained from the evaluation of the response of the measuring element to at least one single pulse by determining transient states of the thermal measuring element during the imposed pulse. From the transient states the measured value of the gas concentration in the environment of the measuring element can be derived, by means of accessible electric measured variables.

The present invention is based on the fact that it is possible to supply thermal measuring elements with energy by pulses and to obtain a measured value of the gas concentration in the environment of the measuring element from the evaluation of the response of the measuring element to the individual feed pulse. Transient states of the thermal measuring element are determined for this by means of accessible electric measured variables during an imposed pulse before a stable end value of the particular measured variable is reached. The measurement is preferably performed periodically.

Transient states of thermal measuring elements are defined in the sense of the present invention primarily as physical or chemical properties of the thermal measuring elements that may appear briefly when thermal measuring elements are not in a thermal equilibrium. This happens, for example, at times that are close to changes in an imposed power, when these changes take place so rapidly that quasi-stationary changes in state in the volume of the thermal measuring elements are practically ruled out. This happens especially in case of pulsed energy supply.

Due to the technical improvement of the catalytic pellistor beads, the stability of their sensitivity has improved markedly compared to the earlier state of the art. In addition, pellistors are now known whose thermal mass is so small that they are suitable for transient measurements with short time constants. The process according to the present invention can, moreover, also be carried out with other gas-sensitive thermal measuring elements.

The thermal measuring element may advantageously be a catalytically active pellistor. This has a catalytic layer that contains catalysts, for example, Rh, Pt, Pd or other catalytically active elements or compounds of elements or combinations thereof. Advantageous carrier materials, which are used to support the catalysts, are aluminum oxide, zirconium oxide, magnesium oxide or other carrier substances or mixtures thereof. It was found that catalytic reaction of gases to be detected can already take place at a temperature between 100° C. and 570° C. with pellistors that contain the above-mentioned materials. This is a decisive advantage concerning long-term stability and power consumption.

To carry out the process according to the present invention, a catalytically active pellistor is preferably to be used whenever a chemical reaction of the gases being measured shall lead to a change in the resistance of the thermal element.

However, the thermal measuring element may also be a catalytically inactive pellistor. This inactive pellistor is preferably likewise heated for the measurement to a temperature between 100° C. and 570° C.

A catalytically inactive pellistor is preferably to be used whenever thermal properties of the gas being measured shall lead to a change in the resistance of the thermal element without a catalytic reaction being necessary.

The thermal element may advantageously be a combination of a catalytically active pellistor with an inactive pellistor, which are temporarily heated to a temperature between 100° C. and 570° C.

The process according to the present invention can be carried out, in principle, with most thermal measuring elements, i.e., for example, microstructured elements, Pt 100 or air-core coils, whose measurable effect is that a change in temperature leads to a change in the electric resistance.

The present invention comprises a process for measuring a gas concentration with at least one thermal measuring element, which is operated by pulses, and in which a measured value of the gas concentration in the environment of the measuring element is obtained from the evaluation of the response of the measuring element to at least one single pulse, characterized in that transient states of the thermal measuring element, from which the measured value of the gas concentration in the environment of the measuring element can be derived, are determined during the imposed pulse on the basis of accessible electric measured variables. The process according to the present invention comprises only two phases, a measuring phase and a rest phase. A variable electric power $P_{measurement}$ that is necessary for the measuring operation is fed in during the measurement phase (duration $T_{measurement}$). A variable or constant electric power $P_{rest}$ necessary for the rest operation of the thermal element is fed during the rest phase (duration $T_{rest}$). $P_{rest} < P_{measurement}$ is always true and advantageously $T_{rest} > 0.5 * T_{measurement}$. It is also possible to insert markedly longer phases of rest to save energy.

The process may also be carried out with a plurality of thermal measuring elements, for example, pellistors, in which case a pulsed two-bead operation can be advantageously embodied.

However, an essential advantage of the process according to the present invention sufficient to compensate environmental effects and to reliably uncouple them from the effect of the target gas proper, whose concentration is to be measured.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
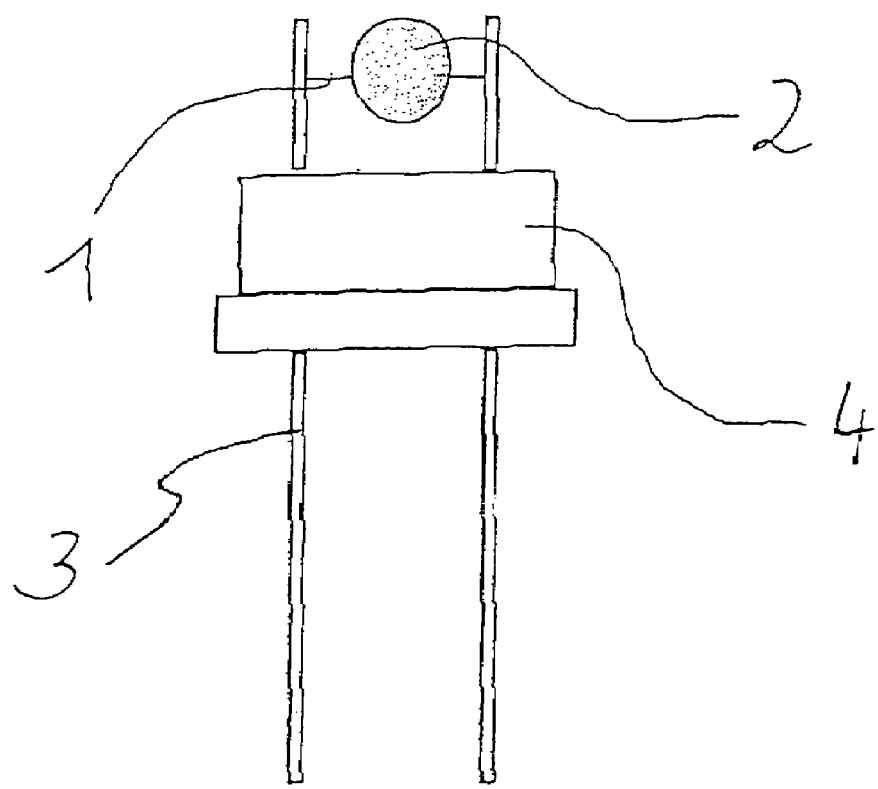
FIG. 1 is a pellistor suitable for carrying out the process.

Referring to the drawings in particular, FIG. 1 shows a pellistor suitable for carrying out the process according to the invention. This pellistor comprises a platinum coil 1, on which a catalytically coated bead 2 is located. The platinum coil 1 is connected to contact pins 3, which lead through a base 4.

Figure 2:
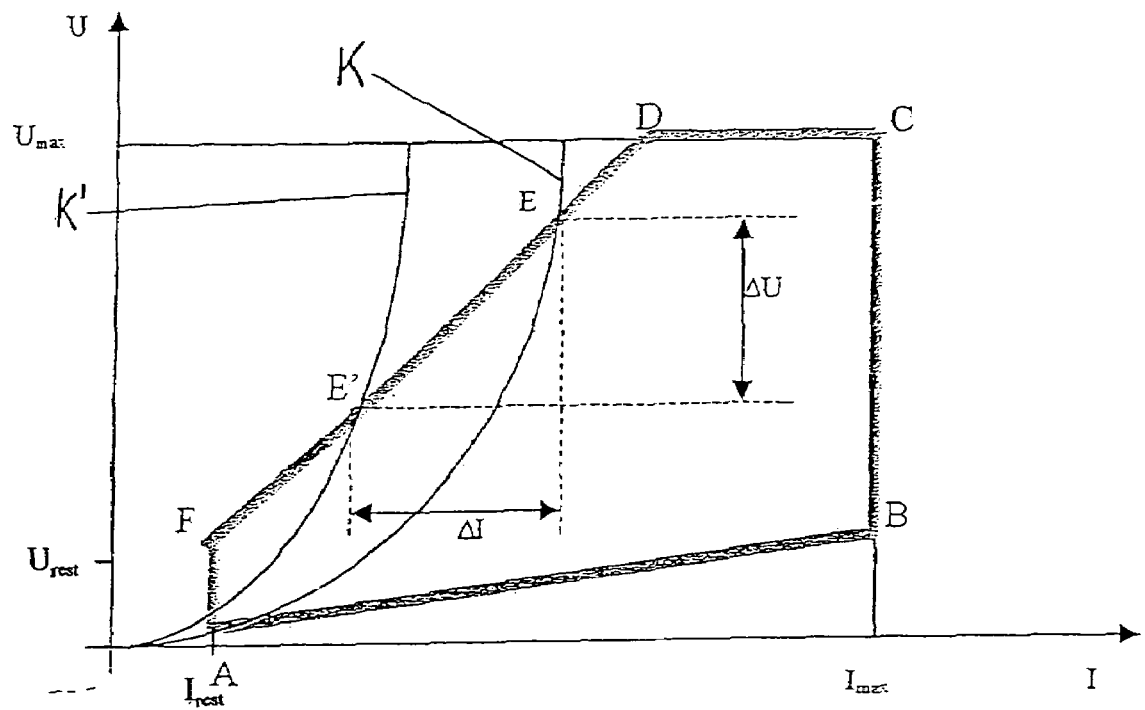
FIG. 2 is a U-I curve of a pellistor operated according to the present invention.

FIG. 2 shows a U-I curve in the family of characteristics of a pellistor operated according to the present invention, as it is passed through during a pulse. The pellistor is supplied with $I_{rest}$ before the pulse, during the rest phase. This current is sometimes sufficient to determine the resistance of the pellistor and thus its temperature. The resistance reached at the end of the rest phase at point A is designated by $R_{cold}$. The vertical section F-A shows that cooling of the pellistor takes place during the rest phase and the voltage drops with the resistance at a constantly low $I_{rest}$.

A constant heating current $I_{max}$ is fed at the beginning of the measurement phase, which causes a jump from A to B in the family of characteristics. This current leads to heating of the pellistor and consequently to an increase in the electric resistance, illustrated by section B-C.

The voltage is limited by the circuitry to a maximum $U_{max}$. When this maximum is reached, the heating output that is the maximum during a pulse is reached at the same time at point C. However, the temperature and hence the resistance continue to increase. As a result, the current decreases at constant voltage $U_{max}$ until a preset adjustable resistance $R_{hot}$ is reached at point D.

The current and the voltage are adjusted beginning from point D by adjustment of the constant resistance such that the resistance of the pellistor is maintained constantly at $R_{hot}$. The thermal equilibrium of the pellistor with its environment is set during this phase. This process takes place on the linear section D-F of the curve. This section intersects the family of curves K, K', which describes the U-I characteristic of the pellistor in quasi-stationary operation as a function of the target gas concentration. The setting of the thermal equilibrium of the pellistor will therefore end in the family of characteristics at the intersection of the linear section D-F with the characteristic K, K' belonging to the particular target gas concentration. The stationary working point of the pellistor, which belongs to a certain temperature and target gas concentration, is reached in this case. Point E marks such a working point in the absence of the target gas, and point E' marks a stationary working point at a certain target gas concentration. The measuring phase can be concluded at the latest when the stationary state is reached and the rest phase begins again.

The essence of this exemplary embodiment is that at least one thermal measuring element is heated until a preset resistance $R_{hot}$ is reached, the thermal measuring element is subsequently operated at this preset resistance by means of a constant resistance control, the current and voltage values necessary for the controlled operation of the thermal measuring element are determined, and stationary end values, which the measured current and voltage values seek to reach, are determined from these measured values.

It is possible without problems to preselect the preset resistance $R_{hot}$, up to which at least one thermal measuring element is heated, in a gas species-specific manner. The species of a gas present can thus be determined by carrying out the measurement with different preselected resistances $R_{hot}$ one after another.

The measurement phase can advantageously be kept shorter if the variables describing the stationary working point are determined by extrapolation. Measured values that can be obtained during the controlled phase after reaching the hot resistance $R_{hot}$ are used to support the extrapolation.

In a typical embodiment, the duration of the measuring phase $T_{measurement}$ is between 10 msec and 3,500 msec the duration of the rest phase $T_{rest}$ is between 50 msec and several seconds. Measuring phases between 100 msec and 1,500 msec are especially advantageous.

An exponential extrapolation is advantageously performed to determine the stationary end values. The difference between the stationary end values of the current ($\Delta I$) and the voltage ($\Delta U$), which is obtained when one measurement is carried out in the absence of the target gas and one measurement is performed at a target gas concentration to be determined, is advantageously used as an indicator of the concentration of a target gas to be determined.

Figure 3:
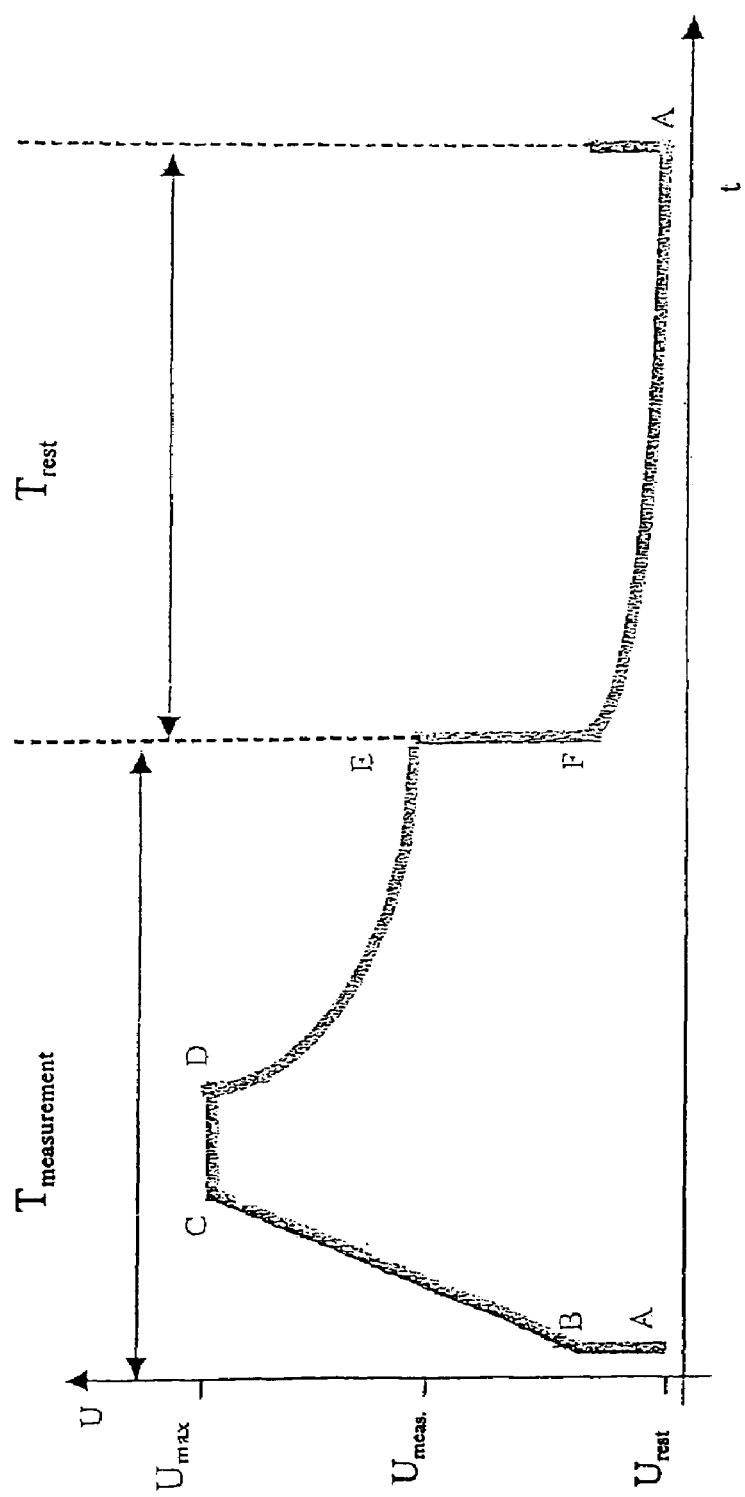
FIG. 3 is a U-t curve of a pellistor operated according to the present invention.
Figure 4:
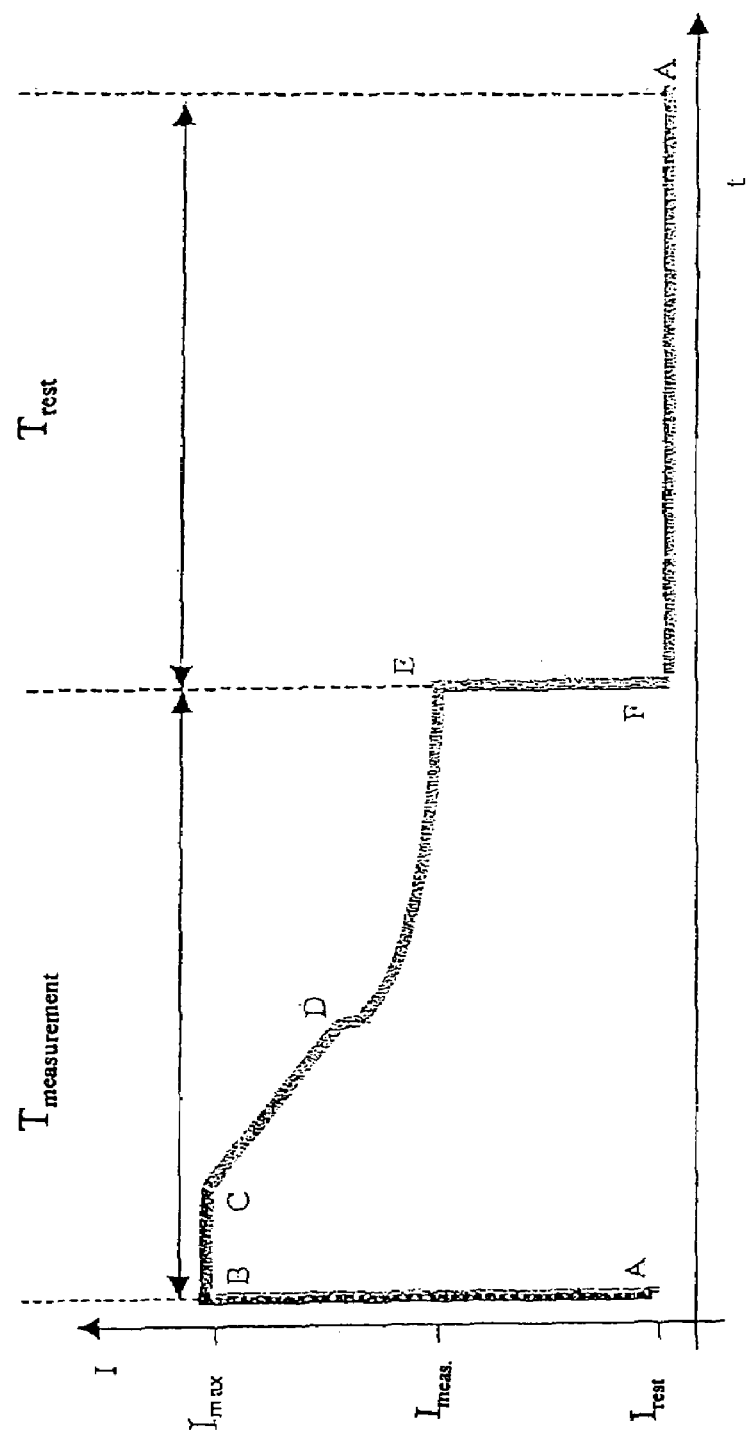
FIG. 4 is an I-t curve of a pellistor operated according to the present invention.

FIG. 3 and FIG. 4 show the voltage and current curves belonging to the above-described cycle for a pellistor operated according to the present invention as a function of time. Sections B-C and C-D are shown as linear sections for simplicity's sake. However, all curve sections having a finite rise may have curvatures in practice and be included in the determination of transient states according to the present invention. Section D-E or D-E' is a range that is of particular interest for the evaluation. The electric variables U and I asymptotically approach an end value each, which describes the stationary working point of the pellistor. The target gas concentration can be determined from the position of this working point. The measurements necessary for this can be terminated when sufficient information or a sufficient amount of measured values that permit the working point to be determined by extrapolation are available.

Various special cases are conceivable when the process according to the present invention is carried out.

For example, the maximum current $I_{max}$ fed in may be equal to the measuring current. The operation then takes place in the constant-current operation during the pulse. The temperature necessary for the operation of the thermal measuring element is generated by means of a constant current. The measured variable is the voltage, its course during the measuring phase and the end value, which becomes established at the end of the measuring phase. This can in turn be determined by extrapolation.

In another special case, $U_{max}$ corresponds to the measuring voltage. The operation is then carried out in the constant-voltage operation during the pulse. The temperature necessary for the operation of the thermal measuring element is generated by means of a constant voltage. The measured variable is the current, its course during the measuring phase and the end value that becomes established at the end of the measuring phase. This can in turn be determined by extrapolation.

The thermal measuring element is switched off completely during the rest phase in a third special case. No measurements are performed.

The current and/or voltage drop over gas-sensitive thermal measuring elements, especially over a pellistor, are used as measured variables in the process being described, and the course of these variables over time is determined. Derived variables, e.g., the resistance, the temperature, the electric heating output, the rates of heating and cooling, a chemical heating output, a thermal resistance and other physical variables can be derived from this and included in evaluations.

The time course of the current and voltage curves and the end values that may possibly become established depend on ambient conditions such as the ambient temperature, air pressure, relative humidity and the gas composition. At the same time, information can be obtained on the gas composition and the ambient conditions by measuring these time courses.

The process, which can be called a transient method according to the present invention, can be embodied with different evaluation methods. It is essential that the evaluation of the response of a thermal measuring element to a current-voltage pulse fed reveals transient states of the thermal measuring element, from which a prevailing target gas concentration and interference variables related to the environment can be unambiguously inferred at the same time.

As a result, only one measuring element is necessary, with which the measurement proper and a necessary compensation of interference effects can be carried out. Very good results can be obtained with a pellistor, which has a catalytically coated bead with a volume of less than 2 mm$^3$, at a power consumption of less than 80 mW, and even markedly lower power consumptions, e.g., below 10 mW, can be achieved by changing the pulse-duty factor. Reaction temperatures that are below 570° C. can be reached on the catalyst surface for the important target gas methane by means of corresponding material combinations, for example, Rh, Pt or Pd as the catalysts and aluminum oxide, zirconium oxide or magnesium oxide as the carrier materials, which are used to support the catalysts. The measurement takes place so rapidly and converts so little gas that the process becomes independent from transport processes, i.e., the diffusion of products and educts.

For example, the derivations of the current and voltage curves over time, time integral, frequency analyses or determination of the percentage of harmonics in the spectrum of the curves recorded can be used to evaluate the recorded curves.

Changes in activity in a catalytically active thermal measuring element, as they may occur due to aging phenomena or chemical poisoning, can advantageously also be determined with the process according to the present invention by determining changes in the transient behavior of the thermal measuring element.

Figure 5:
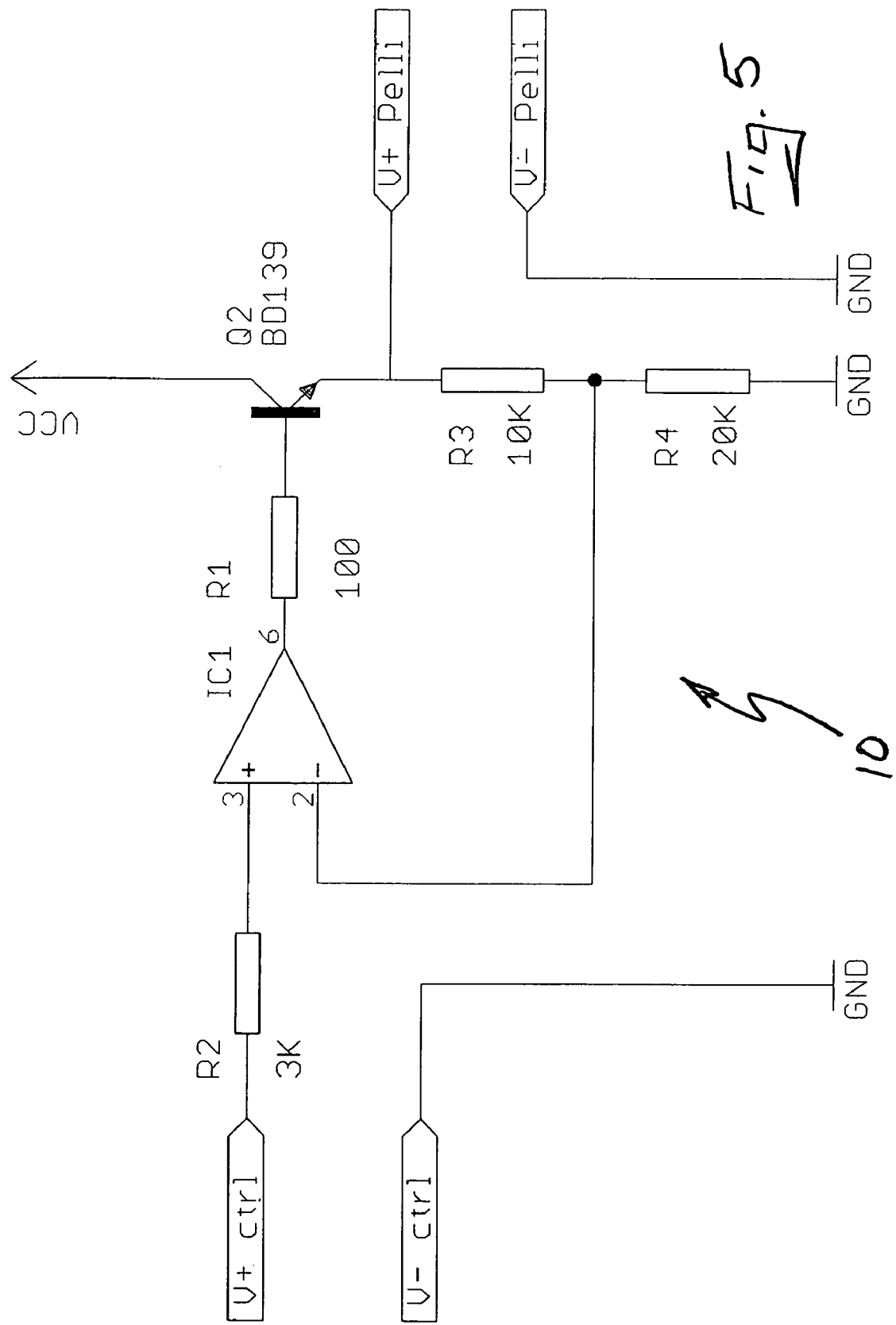
FIG. 5 is a lock-in amplifier that may be used for a lock-in process as a feature in combination with the other process features according to the present invention to increase the accuracy of measurement.

To increase the accuracy of measurement, the process according to the present invention can be combined with a lock-in process. While the sensor is modulated with a fixed frequency the response is a signal carrying components of the same frequency and harmonic multiples thereof with fixed phases related to the modulation. The noise, however, is uncorrelated. A lock-in process is a way to filter the response signal to exactly the same frequency as the modulation signal (or a harmonic multiple) and a fixed phase in relation to it. The bandwidth passing the lock-in process is a very small fraction of the signal bandwidth so that the total noise is reduced to the same fraction. A lock-in amplifier is shown in FIG. 5. This amplifier circuit generally designated 10 is connected to the control current-voltage pulse (V+ctrl, V−ctrl) and pellistor contacts (V+Pelli, V−Pelli) and includes reistors R1-R4, operational amplifier or integrated circuit IC1 and transistor/amplifier Q2. Although such electronic circuits are quite suitable for this purpose, a lock-in process can also be performed by software that processes the digitized response signal. If the sensor is heated periodically with a frequency close to the inverse of its time constant then the resistance of the wire will be a periodic function with the modulation frequency and a fixed phase shift very similar to a sinusoid with little contributions from harmonic frequencies. If a catalytic reaction takes place during the time fractions when the bead is hot the resistance will be influenced by the additional heat. This will contribute considerably to the amplitudes and phases of the harmonic signals. A combination of these harmonic amplitudes give a value representative for the concentration of the reactants.

While specific embodiments of the invention have been shown and described in detail to illustrate the application of the principles of the invention, it will be understood that the invention may be embodied otherwise without departing from such principles.

What is claimed is:

1. A process for measuring gas concentration, the process comprising:

providing a thermal measuring element;

operating said thermal measuring element by applying pulses; and obtaining a measured value of the gas concentration in the environment of the measuring element from the evaluation of a response of the measuring element to at least one single pulse by determining transient states of the thermal measuring element during the imposed pulse, from which transient states the measured value of the gas concentration in the environment of the measuring element can be derived from accessible electric measured variables, the thermal measuring element being heated until a preset resistance is reached, the thermal measuring element being subsequently operated at this preset resistance by means of a constant resistance control, the current and voltage values necessary for the controlled operation of the thermal measuring element being determined, and stationary end values, which the determined current and voltage values seek to reach, are determined from these determined values, the determination of the stationary end values being performed by exponential extrapolation, which is based on measured values of the current and/or voltage, which are obtained during the operation of the thermal measuring element by means of a constant resistance control, exponential extrapolation being performed to determine the stationary end values.

* * * * *